US008293278B2

(12) United States Patent
Tsukimura

(10) Patent No.: US 8,293,278 B2
(45) Date of Patent: Oct. 23, 2012

(54) COMPOSITIONS AND METHODS FOR INHIBITING REPRODUCTION IN TADPOLE SHRIMP

(75) Inventor: Brian K C Tsukimura, Fresno, CA (US)

(73) Assignee: Fresno California State University, Fresno, CA (US)

( * ) Notice: Subject to any disclaimer, the term of this patent is extended or adjusted under 35 U.S.C. 154(b) by 340 days.

(21) Appl. No.: 12/619,638

(22) Filed: Nov. 16, 2009

(65) Prior Publication Data

US 2010/0129458 A1     May 27, 2010

Related U.S. Application Data

(60) Provisional application No. 61/117,050, filed on Nov. 21, 2008.

(51) Int. Cl.
    *A01K 97/04*        (2006.01)
    *A61K 9/14*         (2006.01)
    *A61K 31/22*        (2006.01)

(52) U.S. Cl. .......... 424/490; 424/84; 424/489; 514/549; 426/1; 426/805

(58) Field of Classification Search ........................ None
See application file for complete search history.

(56) References Cited

U.S. PATENT DOCUMENTS

| 3,889,007 | A | 6/1975 | Gunter et al. |
| 5,161,481 | A | 11/1992 | Laufer |
| 2002/0086089 | A1 * | 7/2002 | Kurzinger ........................ 426/2 |

FOREIGN PATENT DOCUMENTS

WO     WO8701587     3/1987

OTHER PUBLICATIONS

Sigma-Aldrich L3906, 2 pages.*
Borst, D.W. and Laufer, H., Methyl Farnesoate; a JH-like Compound in Crustaceans. Recent Advances in Comparative Arthropod Morphology, Physiology and Development. Ed: A.P. Gupta. Rutgers University Press, New Brunswick, NJ (1990) pp. 35-60.
Borst, D.W. and Tsukimura, B., Quantification of methyl farnesoate levels in hemolymph by high-performance liquid chromatography, Journal of Chromatography, 545 (1991) 71-78.
Borst, D.W., Tsukimura, B., Laufer, H. and Couch, E., Regional Differences in Methyl Farnesoate Production by the Lobster Mandibular Organ, Biol. Bull. 186: 9-16 (Feb. 1994).
Borst, D.W., Ogan, J., Tsukimura, B., Claerhout, T. and Holford, K.C., Regulation of the Crustacean Mandibular Organ, Amer. Zool., 41: 430-441 (2001).
Claerhout, T., Bendena, W., Tobe, S.S. and Borst, D.W., Characterization of Methyl Transferase Activity in the Mandibular Organ of the American Lobster, Homarus americanus, Biol. Bull. 191: 304 (Oct. 1996).
Feyereisen, R., Pratt, G.E., and Hamnett, A.F., Enzymatic Synthesis of Juvenile Hormone in Locust Corpora Allata: Evidence for a Microsomal Cytochrome P-450 Linked Methyl Farnesoate Epoxidase. Eur. J. Biochem. 118: 231-238 (1981).
Fry, L.L. and Mulla, M.S., Effect of Drying Period and Soil Moisture on Egg Hatch of the Tadpole Shrimp (Notostraca: Triopsidae), J. Econ. Entomol. 85(1): 65-69 (Feb. 1992).
Fry-O'Brien, L.L. and Mulla, M.S., Optimal Conditions for Rearing the Tadpole Shrimp, *Triops longicaudatus* (Notostraca: Triopsidae), A Biological Control Agent Against Mosquitoes, J. Amer. Mosquito Control Association, 12 (3): 446-453 (1996).
Grigarick, A.A., General Problems with Rice Invertebrate Pests and Their Control in the United States, Protection Ecology 7: 105-114 (1984).
Grigarick, A.A., Lynch, J.H. and Way, M.O., Controlling Tadpole Shrimp, California Agriculture 393(3): 12-13 (Mar.-Apr. 1985).
Hillyard, S.D. and Vinegar, A., Respiration and Thermal Tolerance of the Phyllopod Crustacea *Triops longicaudatus* and *Thamnocephalus platyurus* Inhabiting Desert Ephermeral Ponds, Physiology Zoology 45(3): 189-195 (Jul. 1972).
Homola, E. and Chang, E.S., Distribution and Regulation of Esterases That Hydrolyze Methyl Farnesoate in *Homarus americanus* and Other Crustaceans, General and Comparative Endocrinology 106: 62-72 (1997).
Laufer, H., Borst, D., Baker, F.C., Carrasco, C., Sinkus, M., Reuter, C.C., Tsai, L.W. and Schooley, D.A., Identification of a Juvenile Hormone-Like Compound in a Crustacean, Science 235: 202-205 (1987).
Laufer, H., Sagi, A, Ahl, J.S.B., Homola, E., Methyl Farnesoate Appears to be a Crustacean Reproductive Hormone, Invertebrate Reproduction and Dev. 22: 1-3 (1992) 17-20.
Laufer, H., Biggers, W.J., and Ahl, J.S.B., Stimulation of Ovarian Maturation in the Crayfish *Procambarus clarkii* by Methyl Farnesoate, General Comparative Endocrinology 111: 113-118 (1998).

(Continued)

*Primary Examiner* — Daniel Sullivan
*Assistant Examiner* — Kyle Purdy

(57) ABSTRACT

Compositions, methods for forming compositions, and methods for using compositions for reducing tadpole shrimp populations in temporary pools using the hormone methyl farnesoate. Compositions can include a dry base having a bulk ingredient, a viscous additive having an oily compound, a saline solution, and preparation having an effective amount of phospholipid-encapsulated methyl farnesoate. The composition can be formed by combining the dry base and the viscous additive into a first mixture and adding all or a portion of the saline solution to form a crumbly consistency. Then, the methyl farnesoate preparation can be added. The composition may then be formed into a plurality of particles having shapes and sizes for consumption by the tadpole shrimp. In use, the particles may be dispensed prior to, or immediately after, the temporary pools are flooded with water. The particles may be formed such that they can withstand exposure to water for between about 4 to about 14 days.

9 Claims, No Drawings

OTHER PUBLICATIONS

Laufer, H. and Biggers, W.J., Unifying Concepts Learned from Methyl Farnesoate for Invertebrate Reproduction and Post-Embryonic Development, Amer. Zool. 41: 442-457 (2001).

Linder, C.J. and Tsukimura, B., Inhibitory Effects of Methyl Farnesoate (MF) on the Reproductive Development of Tadpole Shrimp (TS), *Triops longicaudatus*, Amer. Zool. 40: 276A (2000).

Nelson, W., Juvenilizing Effects of Methyl Farnesoate on Reproduction and Development in the Riceland Tadpole Shrimp, *Triops longicaudatus*. Department of Biology, Master's Thesis, California State University, Fresno (Aug. 2005).

Riley, L.G. and Tsukimura, B. Yolk Protein Synthesis in the Riceland Tadpole Shrimp, *Triops longicaudatus*, Measured by In Vitro Incorporation of 3H-Leucine, The Journal Experimental Zoology 281: 238-247 (1998).

Rosenberg, L.E., Fairy Shrimps in California Rice Fields, Letters to the Editor, Science vol. 104 No. 2692:111-112. (1946).

Seaman, M.T., Kok, D.J. Von Schlichting, B.J. and Kruger A.J., Natural Growth and Reproduction in *Triops granarius* (Crustacea: Notostraca), Hydrobiologia 212: 87-94 (1991).

Tobe, S.S., Young, D.A. and Khoo, H.W., Production of Methyl Farnesoate by the Mandibular Organs of the Mud Crab, *Scylla serrata*: Validation of a Radiochemical Assay, General and Comparative Endocrinology 73: 342-353 (1989).

Tsukimura, B. Crustacean Vitellogenesis: Its Role in Oocyte Development, Amer. Zool. 41: 465-476 (2001).

Tsukimura, B. and Kamemoto, F.I, In Vitro Stimulation of Oocytes by Presumptive Mandibular Organ Secretions in the Shrimp, *Penaeus vannamei*, Aquaculture 92: 59-66 (1991).

Tsukimura, B., Nelson, W.K. and Linder, D.J., Inhibition of Ovarian Development by Methyl Farnesoate in the Tadpole Shrimp, *Tripos longicaudatus*, Comparative Biochemistry and Physiology, Part A 144: 135-144 (2006).

Organic Foods Protection Act of 1990 (7 U.S.Code including amendments as of Jan. 1, 2004), Sections 6501-6522, Organic Farming Compliance Handbook: A Resource Guide for Western Region Agricultural Professionals.

Conklin, D.E., Devers, K., Shleser, R.A., Initial Development of Artificial Diets for the Lobster, *Homarus americanus*, J. World Aquac. Soc. 6: 237-248 (1975).

Godfrey, L.D., UC IPM Pest Management Guidelines: Rice; Tadpole Shrimp, *Triops longicaudatus* UC ANR Publication 3465 (2005) (http://www.ipm.ucdavis.edu/PMG/r682500111.html).

Tsukimura, B. and Mutters, R.G., Control of Tadpole Shrimp by Methyl Farnesoate Inhibition of Reproduction, California Agricultural Technology Institute, CSU Fresno, ARI Pub. #02-028-12.

New Biological Control Proves Effective Against Tadpole Shrimp, CSU Agricultural Research Initiative (ARI), (May 2008) http://www.fresnostatenews.com/2008/05/BiologicalControl.htm.

Linder, C.J., Ovarian Development Inhibition by Methyl Farnesoate in the Tadpole Shrimp, *Triops longicaudatus*, Department of Biology, Master's Thesis, California State University, Fresno (May 2001).

Rudnick, D., Veldhuisen, T., Tullis, R., Culver, C., Hieb, K. and Tsukimura, B., A Life History Model for the San Francisco Estuary Population of the Chinese Mitten Crab, *Eriocheir sinensis* (Decapoda: Grapsoidea), Biological Invasions 7: 333-350 (2005).

Tsukimura, B., Bender, J.S. and Linder, C.J., Development of an Anti-Vitellin ELISA for the Assessment of Reproduction in the Ridgeback Shrimp, *Sicyonia ingentis*, Comparative Biochemistry and Physiology Part A, 127: 215-224 (2000).

Borst, D.W., Tsukimura, B., and Frinsko, M., Methyl Farnesoate Levels in the Crayfish, *Orconectes virilis*, Freshwater Crayfish VIII, pp. 462-474, Ed: R.P. Romaire, Louisana State Printing Office, New Orleans (1995).

Tsukimura, B., and Borst, D.W., Regulation of Methyl Farnesoate in the Hemolymph and Mandibular Organ of the Lobster, *Homarus americanus*, General and Comparative Endocinology 86: 297-303 (1992).

Borst, D.W. and Tsukimura, B., Methyl Farnesoate Levels in Crustaceans, In: Insect Juvenile Hormone Research, pp. 27-35 (1992). B. Mauchamp, F. Couillaud and J.C. Baehr, Eds. Institut National de la Recherche Agronomique, Paris, France.

Abdu, U., Takac, P., Laufer, H., and Sagi, A., Effect of Methyl Farnesoate on Late Larval Development and Metamorphosis in the Prawn *Macrobrachium rosenbergii* (Decapoda, Palaemonidae): A Juvenoid-like Effect?, Biol. Bull. 195: 112-119 (Oct. 1998).

Abdu, U., Barki, A., Karplus, I., Barel, S. Takac, P. Yehezkel, G., Laufer, H., and Sagi, A., Physiological Effects of Methyl Farnesoate and Pyriproxyfen on Wintering Female Crayfish, *Cherax quadricariatus*, Aquaculture 202: 163-175 (2001).

Borst, D.W., Laufer, H., Landau, M., Chang, E.S., Hertz, W.A., Baker, F.C. and Schooley, D.A., Methyl Farnesoate and its Role in Crustacean Reproduction and Development, Insect Biochem. vol. 17, No. 7, pp. 1123-1127 (1987).

Charmantier, G., Charmantier-Daures, M. and Aiken, D.E., Larval Development and Metamorphosis of the American Lobster *Homarus americanus* (Crustacea, Decapoda): Effect of Eyestalk Ablation and Juvenile Hormone Injection, General and Comparataive Endocrinology 70: 319-333 (1988).

Conklin, D.E., Devers, K., and Bordner, C., Development of Artificial Diets for the Lobster, *Homarus americanus*,Proc. World Maric Soc., 8: 841-852 (1977).

Ding, Q., and Tobe, S.S., Production of the Farnesoic Acid and Methyl Farnesoate by Mandibular Organs of the Crayfish, *Procambrus clarkii*, Insect Biochem, vol. 21, No. 3, pp. 285-291 (1991).

King, L.E., Ding, Q., Prestwich, G.D., and Tobe, S.S., The Characterization of a Haemolymph Methyl Farnesoate Binding Protein and the Assessment of Methyl Farnesoate Metabolism by the Haemolymph and Other Tissues from *Procambrus clarkii*, Insect Biochem. Molec. Biol. vol. 25, No. 4, pp. 495-501 (1995).

Kwok, R., Zhang, J.R., and Tobe, SS., Regulation of Methyl Farnesoate Production by Mandibular Organs in the Crayfish, *Procambrus clarkii*: A Possible Role for Allatostatins, Journal of Insect Physiology, 51: 367-378 (2005).

Laufer, H., Takac, P., Ahl, J.S.B., and Laufer, M.R., Methyl Farnesoate and the Effect of Eyestalk Ablation on the Morphogenesis of the Juvenile Female Spider Crab *Libinia emarginata*, Invertebrate Reproduction and Development, 31: 63-68 (1997).

Laufer. H., Ahl, J., Rotllant, G., and Baclaski, B., Evidence that Ecdysteriods and Methyl Farnesoate Control Allometric Growth and Differentiation in a Crustacean, Insect Biochemistry and Molecular Biology, 32: 205-210 (2002).

Nelson, W. and Tsukimura, B., Reproductive Inhibition by Methyl Farnesoate in the Tadpole Shrimp *Triops longicaudatus*, Integ. Comp. Biol. 42(6), 1284 (2002).

Smith, P.A., Clare, A.S., Rees, H.H., Prescott, M.C., Wainwright, G., and Thorndyke, M.C., Indentification of the Methyl Farnesoate in the Cypris Larva of the Barnacle, *Balanus amphitrite*, and its Role as a Juvenile Hormone, Insect Biochemistry and Molecular Biology 30: 885-890 (2000).

Wainwright, G., Webster, S.G., and Rees, H.H., Neuropeptide Regulation of Biosynthesis of the Juvenoid, Methyl Farnesoate, in the Edible Crab, *Cancer pagurus*, Biochem. J. 334: 651-657 (1998).

\* cited by examiner

COMPOSITIONS AND METHODS FOR INHIBITING REPRODUCTION IN TADPOLE SHRIMP

RELATED APPLICATIONS

This application claims the benefit of U.S. Provisional Application No. 61/117,050, filed on Nov. 21, 2008 which is incorporated herein by reference in its entirety.

BACKGROUND OF THE INVENTION

1. Field of the Invention

The present invention generally relates to compositions, methods for forming compositions, and methods of using compositions for hormonally reducing tadpole shrimp populations. More specifically, embodiments of the present invention relate to processes, methods, and compositions for organically inhibiting tadpole shrimp reproduction to prevent damage to agricultural crops, including rice.

2. Background and Description of Related Art

*Triops longicaudatus*, commonly known as the tadpole shrimp, is a small pest which inhabits temporary pools. Adult tadpole shrimp will deposit eggs in the bed of such pools, and the eggs eventually become cysts which are highly resistant to harsh physical conditions (such as, for example, dehydration and extreme temperatures). These cysts have the ability to remain viable in a dormant state for several years in dry, unflooded soil. Upon the flooding of the soil with water, many cysts will activate and begin to hatch.

The rapid growth and reproduction of tadpole shrimp have created a persistent problem in infested rice fields which are typically flooded prior to the planting of the rice crop. In general, tadpole shrimp hatch within two or three days after the cysts are exposed to a sufficient amount with water. Upon hatching, the tadpole shrimp begin to forage for organic material to feed on. The foraging behavior, including digging and agitating the soil, often dislodges or prevents young rice cotyledons from rooting in the ground. This disruption can create yield losses amounting to 20% or greater for affected rice fields. Although tadpole shrimp foraging behavior can disrupt the rice seedlings in the process of rooting, once the roots are well established in the soil, the tadpole shrimp pose minimal, if any, threat of harm or injury to the rice plant and resulting crop yields.

Because the tadpole shrimp has become highly adaptable to survive through extreme environmental conditions, there is no simple way to eliminate them from the environment. Tadpole shrimp eggs and cysts have proven to survive in a desiccated state for a number of years. Additionally, not all tadpole shrimp eggs hatch the first time the given area is flooded, but may instead hatch during a subsequent flooding of the area. Further, the eggs are easily spread by modern farming techniques, making containment of the tadpole shrimp to certain areas very difficult. Elimination of tadpole shrimp is also exacerbated by their high reproductive fecundity; tadpole shrimps can begin developing oocytes in as little as four days, and are further capable of producing hundreds of eggs.

Conventional attempts at controlling tadpole shrimp population include the application of copper sulfate. However the use of copper sulfate is not considered to be environmentally sustainable, and its use is becoming disfavored. The United States Environmental Protection Agency has categorized copper sulfate as a class I hazardous toxin, and its use may be prohibited in the near future. Moreover, the presence of copper sulfate residue in the soil is unfavorable to rice growing conditions.

Recent scientific studies have shown that the hormone methyl farnesoate [methyl-(2E,6E,10E)-3,7,11-trimethyl-dodecatri-2,6,10-eneoate] (sometimes referred to herein as "MF") inhibits growth, development, and gamete production in some pests, such as tadpole shrimp. Studies have shown that methyl farnesoate reduces sexual development of tadpole shrimp. Methyl farnesoate is easily oxidized into farnesoic acid and concentrations of methyl farnesoate rapidly decrease when exposed to oxidizing agents in the environment. Because methyl farnesoate oxidizes quickly and therefore will not build up large concentrations in the soil, and because it is a fatty acid, it is not considered to be harmful to the environment or adversely affect crop production. However, it is for these same reasons that administration of methyl farnesoate is difficult to administer.

U.S. Pat. No. 5,161,481 concerns using methyl farnesoate to increase larval production in white shrimp, or *Litopenaeus* (as *Penaeus*) *vannamei*, in marine environments. The white shrimp of the '481 patent belong to the Class: Malacostraca, Subclass: Eumalacostraca, Superorder: Eucarida, Order: Decepoda, Suborder: Dendrobranchiata, Superfamily: Penaeoidea, and Family: Penaeidae, which are marine shrimp. In contrast, the tadpole shrimp referred to in the present application belong to the Class: Branchiopoda, Subclass: Phyllopoda, and Order: Notostaca, which are fresh water organisms. The different biological characteristics are believed to explain why the same or similar compounds, and particularly methyl farnesoate, produce different reproductive effects on these different organisms.

It is therefore desirable to provide economical and environmentally friendly compositions and methods for preventing crop loss due to tadpole shrimp population without the use of copper sulfate.

SUMMARY OF THE INVENTION

Embodiments of the present invention relate to processes, methods and compositions for making and delivering the hormone methyl farnesoate to inhibit ovarian development and the development of eggs in tadpole shrimp in fresh water environments.

In one aspect, the invention concerns a composition for inhibiting tadpole shrimp reproduction which may include: a dry base comprising a bulk ingredient and a binder; a viscous additive comprising an oily compound; a saline solution comprising an evaporative fluid and a salt; and a preparation comprising an effective amount of methyl farnesoate encapsulated in phospholipids. In some embodiments, the composition may include at least about 0.0001% methyl farnesoate by weight. In some embodiments, the composition may include less than about 0.001% methyl farnesoate by weight.

In some embodiments, the composition may include about 90 parts of the dry base to between about 5 parts and about 10 parts of the viscous additive. In some embodiments, the composition may include about 90 parts of the dry base to between about 1 part and about 5 parts of the salt. In some embodiments, the composition may have a moisture content of between about 5% and about 18%. In some embodiments, the composition may have a moisture content of between about 12% and about 25%. In some embodiments, the composition may have a moisture content of less than about 25%. In some embodiments, the composition may have a pH value of between about 7.8 and about 8.0.

In some embodiments, the bulk ingredient may include flour, gluten, alphacel, casein, and/or starch. In some embodiments, the binder may include albumin, lecithin, and/or starch. In some embodiments, the dry base may also include a nutritional supplement including flour, albumin, starch, casein, and/or lecithin. In some embodiments, the oily compound may include fish oil and/or vegetable oil. In some embodiments, the composition may also include an attractant including lecithin, casein, vitamin E acetate, cholesterol, fish extract, fish byproduct, crustacean extract, crustacean byproduct and/or organic matter. In some embodiments, the composition may also include a vitamin including inositol, ascorbic acid, para-amino benzoic acid, niacin, D-calcium, riboflavin, Folic acid, thiamine mononitrate, pyridoxine hydrochloride, butylated hydroxyanisole, biotin, and/or vitamin B-12.

In some embodiments, the salt may include sodium chloride, sodium phosphate, calcium phosphate, calcium carbonate, potassium phosphate, potassium sulphate, potassium chloride, potassium iodide, magnesium oxide, manganese carbonate, citric acid, ferric citrate, zinc carbonate, and/or cupric carbonate. In some embodiments, the salt may include, by weight, about 3% sodium chloride, about 2% sodium phosphate, about 73% calcium phosphate, about 2% calcium carbonate, about 8% potassium phosphate, about 2% magnesium oxide, and about 7% potassium sulphate. In some embodiments, the salinity of the saline solution may be between about 10 ppt and about 45 ppt.

In some embodiments, the preparation may also include a pre-liposome such as L-alpha-phosphatidylcholine beta-oleoyl-gamma-palmitoyl and cholesterol. In some embodiments, the preparation may also include a solvent such as ethanol and/or dimethyl sulfoxide.

In another aspect, the invention concerns a method of making a composition which may include the steps of: combining to form a homogenous first mixture (i) a dry base comprising a bulk ingredient and a binder and (ii) a viscous additive comprising an oily compound; adding a first portion of a saline solution comprising an evaporative fluid and a salt to the first mixture to form a crumbly consistency; and adding a second mixture comprising a preparation comprising an effective amount of methyl farnesoate encapsulated in phospholipids to said first mixture.

In some embodiments, the preparation may be formed by vigorously agitating the methyl farnesoate, a pre-liposome and a solvent. In some embodiments, the second mixture may be formed by adding a second portion of the saline solution and the preparation. In some embodiments, the second mixture may be formed adding a second saline solution to the preparation. In some embodiments, the method may further include adding additional salt to the first or second mixtures.

In some embodiments, when the first mixture has a moisture content of less than about 25%, the method may further include the step of combining a third portion of the saline solution to the first mixture. In some embodiments, when first mixture has a moisture content of less than about 25%, the method may further include the step of combining a second evaporative fluid to the first mixture. In some embodiments, when the first mixture has a moisture content of greater than about 10%, the method may further include the step of combining a second bulk ingredient to the first mixture.

In some embodiments, the method may further include the step of forming the composition into a plurality of particles. In some embodiments, the particles may be shaped as pellets, orbs, cylinders, nuggets, discs, and crystals. In some embodiments, each of the particles may have a diameter of between about 1 and about 6 millimeters. In some embodiments, the method may further include the step of drying the particles. In some embodiments, the particles may be dried to a moisture content of about 5% and about 20%. In some embodiments, the particles may be dried at a temperature of less than about 50 degrees Celsius. In some embodiments, the method may further include the step of coating the particles to inhibit the rate at which they dissolve when exposed to water.

In another aspect, the invention concerns a method for inhibiting the reproductive activity of tadpole shrimp which can include the step of dispensing a plurality of particles into a field where one of the group comprising the tadpole shrimp, eggs of the tadpole shrimp, cysts of the tadpole shrimp, and combinations thereof are present, where the particles include a dry bulk ingredient, an oily compound, a salt, and methyl farnesoate encapsulated in phospholipids.

In some embodiments, the particles may be dispensed prior to flooding the field with water. In some embodiments, when the density of the particles is sufficiently greater then water, the particles may be dispensed after the flooding of the field with water. In some embodiments, the particles may be dispensed at a concentration of about 2 grams per square foot. In some embodiments, the relative percentages by weight of the dry bulk ingredient and the oily compound is such that the particles remain structurally and chemically stable in the field for between about 4 days and about 14 days after exposure to water.

The effect of prolonged exposure to methyl farnesoate is to prevent the tadpole shrimp from producing new eggs/cysts, thus gradually reducing the tadpole shrimp population over repeated flooding of the temporary pools. It is to be appreciated that application of methyl farnesoate will not prevent the eggs of tadpole shrimp already present in the field from hatching. However, current and successive treatments will drastically reduce successive generations of tadpole shrimp in the field, and ideally eventually eliminate them. Accordingly, rice crop yields will increase and further benefits of use will be seen after successive treatments.

The hormone methyl farnesoate is readily oxidized when exposed to the natural environment. To prevent such oxidation, methyl farnesoate may be encapsulated in liposomes, which serves to prevent oxidation and interactions with any compounds outside the protective layer of phospholipids. By providing the phospholipid-encapsulated ovarian inhibitor methyl farnesoate in a chemically stable composition suitable for ingestion by tadpole shrimp, the population of those organisms can be gradually decreased, thereby increasing the yield of certain crop farming operations. Because methyl farnesoate is a fatty acid and oxidizes quickly, its use as described herein will not pose environmental concerns.

These and other objects, advantages and features of the invention, together with the organization and manner of operation thereof, will become apparent from the following detailed description.

DETAILED DESCRIPTION

The invention, in its various aspects, will be explained in greater detail below. While the invention will be described in conjunction with several exemplary embodiments, the exemplary embodiments themselves do not limit the scope of the invention. Similarly, the examples provided herein do not limit the scope of the invention. Rather the invention, as defined by the claims, may cover alternatives, modifications, and/or equivalents of the exemplary embodiments and/or examples.

It is to be appreciated that although the invention is described in conjunction with reference to inhibiting ovarian development of *Triops longicaudatus*, embodiments of the invention also contemplate inhibiting ovarian development of other members of the Class Branchiopoda, Subclass Phyllopoda, Order Notostaca. Thus, it is to be appreciated that the terms "pests," "target pests," and "tadpole shrimp", while given their ordinary meaning, may be used interchangeably. It is also to be appreciated that although the invention is described in conjunction with reference to application in rice fields, it is embodiments of the invention also contemplate application in any temporary pool where the pests may inhabit. It is further to be appreciated that the terms "pellets" and "particles" may be used interchangeably, and generally refer to small consumable units delivering the methyl farnesoate to the pests.

Exemplary Compositions for Inhibiting Ovarian Development

In some embodiments, the invention concerns a composition for inhibiting tadpole shrimp reproduction that can include a dry base, a viscous additive, a saline solution, and a preparation comprising an effective amount of methyl farnesoate encapsulated in phospholipids. As discussed more fully below, in some embodiments, the composition may be formed into a plurality of pellets having sizes suitable for ingestion by tadpole shrimp, and then dispensed in their habitation areas.

In some embodiments, the dry base can include one or more bulk ingredient(s) and one or more binder(s). In some examples, and without limitation, the bulk ingredients give the subsequently formed pellets bulk or volume so as to prevent them from quickly degrading or dissolving while underwater. The bulk ingredient(s) may be selected to assist in providing a certain level of integrity and bulk to the pellets so that they will maintain a solid or semi-solid state when submersed in water. The bulk ingredients may also be selected so that the pellets have a relative density greater than that of water such that they will sink in a flooded temporary pool and will rest on the soil surface so as to be available to be consumed by the foraging tadpole shrimp.

In some embodiments, the bulk ingredient can be a flour. For example, and without limitation, the bulk ingredient can be wheat flour, white flour, or corn flour. In some embodiments, the bulk ingredient can include additional protein for adding rigidity or structure to the composition. For example, and without limitation, the bulk ingredient can be fortified with gluten and/or casein. In some embodiments, the bulk ingredient can include a cellulose or starchy filler. For example, and without limitation, the bulk ingredient can be fortified with alphacel and/or corn starch. In some embodiments, the bulk ingredient can be a single ingredient. For example, the bulk ingredient can be wheat flour. However, it is to be appreciated that the dry base can include one or more bulk ingredients in varying amounts. For example, and without limitation, the dry base can include flour, gluten, alphacel, casein, and/or starch in varying amounts. It is further to be appreciated that, in accordance with some embodiments of the present invention, the bulk ingredient(s) may include any other commonly used economical substance which can be used to give the final product volume and density.

It is to be appreciated that in some applications, it may be desirable to include nutritive components in the composition for encouraging optimal foraging by the juvenile tadpole shrimp. Thus, in some embodiments, the dry base can further include a nutritional supplement. In some embodiments, the nutritive supplement can include a flour and/or a starch. For example, and without limitation, the nutritive supplement can include white flour and/or corn starch. In some embodiments, the nutritive supplement can include a protein. For example, and without limitation, the nutritive supplement can include casein and/or albumin. In some embodiments, the nutritive supplement can comprise a fat. For example, and without limitation, the nutritive supplement can comprise lecithin. It is to be appreciated that other nutritive supplements are contemplated in accordance with some embodiments of the present invention.

As above, the dry base can also include a binder for providing structure to the composition. In some embodiments, the binder can be albumin, lecithin, and/or starch. However, it is to be appreciated that other binders are contemplated in accordance with some embodiments of the present invention.

It is to be appreciated that the dry base may comprise ingredients that may function as the bulk ingredient, the binder, and/or the nutritional supplement. For example, and without limitation, the dry base may consist of only corn starch, which alone functions as both a bulk and binding agent, and can provide nutritional sustenance to the foraging tadpole shrimp. In other examples, the dry base may consist only of white flour and albumin. In some preferred embodiments, the dry base comprises gluten (wheat), wheat flour and/or corn flour, albumin, alphacel lecithin-soy, corn starch and/or casein. In some other preferred embodiments, the dry base comprises wheat flour, alone or in combination with gluten flour or gluten. In some other preferred embodiments, the dry base comprises comprise gluten flour, alone or in combination with gluten. In some preferred embodiments, the dry base may further be fortified with lecithin, albumin and/or alphacel. In some preferred embodiments, the dry base may further be supplemented with corn starch, casein, and/or lecithin. However, it is to be appreciated that the dry base may comprise other ingredients in accordance with some embodiments of the present invention.

In some embodiments, the viscous additive can include an oily compound. It is to be appreciated that a viscous additive including an oily compound serves to keep the composition in a somewhat crumbly state. As discussed more fully below, in some embodiments, the composition may be formed into a plurality of pellets. In contrast to adding water, which could cause the glutens to over bind and jam a pelleting machine, the oil(s) add viscosity and flexibility to the composition which assists and does not negatively affect the pelleting process.

In some embodiments, the oily compound can be fish oil. For example, and without limitation, the oily compound can be cod liver oil. In some embodiments, the oily compound can be vegetable oil. For example, and without limitation, the oily compound can be corn oil. In some embodiments, the viscous additive can include both fish and vegetable oils. However, it is to be appreciated that the viscous additive can include other oils, in accordance with some embodiments of the present invention.

In some embodiments, the composition may further comprise an attractant to lure the tadpole shrimp to consume the composition. In some embodiments, the attractant can include oil based compounds. For example, and without limitation, the attractant can include fish oil, cod liver oil, cholesterol, and/or vitamin E acetate. However, it is to be appreciated that other attractants known in the art may be used, and are not necessarily limited to oil-based compounds. Thus, in some embodiments, the composition can also include an attractant or bait, such as lecithin, casein, fish byproduct, fish extract, crustacean byproduct, crustacean extract, and/or other organic matter. It is further to be appreciated that the attractants can be provided separately, or can be included in or be the dry base or the viscous additive. For example, and without limitation, the dry base can include attractants such as shrimp by-products or other organic matter. In some examples, the viscous additive can include an attractant such as a fish extract. In other examples, the viscous additive can include cod liver oil, which provides viscosity to the composition and which also functions as an attractant. It is to be appreciated that other attractants, whether oil based or not, and whether included in the dry base or the viscous additive, are contemplated in accordance with some embodiments of the present invention.

In some embodiments, the composition can also include a vitamin for encouraging optimal foraging by the juvenile tadpole shrimp. In some examples, the vitamin may include inositol, ascorbic acid, para-amino benzoic acid, niacin, D-Calcium, riboflavin, Folic acid, thiamine mononitrate, pyridoxine hydrochloride, butylated hydroxyanisole, biotin, and/or vitamin B-12. However, other vitamins are contemplated in accordance with some embodiments of the present invention. It is further to be appreciated that the vitamins can be provided separately, or can be included in or be the dry base or the viscous additive.

It is to be appreciated that in some embodiments, the composition comprises methyl farnesoate which has been encapsulated in phospholipids. It has been determined that the encapsulated methyl farnesoate may be destroyed by shearing forces if it is directly admixed to the dry base, the viscous additive, and/or a combination thereof, thus diminishing the effectiveness of the composition. Thus in some embodiments, and discussed more fully below, a saline solution can be included in the composition to protect the phospholipid-encapsulated methyl farnesoate when it is incorporated into the composition. In some embodiments, the saline solution can comprise a fluid, for example, and without limitation, distilled water, and a salt. It is to be appreciated that the salt helps to prevent the disassociation of the methyl farnesoate and the phospholipids while the fluid helps to add fluidity to the composition while the phospholipid-encapsulated methyl farnesoate is incorporated therein and also may assist in the formation of pellets from the composition.

It is to be appreciated that the amount of fluid in the saline solution should be sufficient to reduce shearing forces during the incorporation of the phospholipid-encapsulated methyl farnesoate in the composition but not so great so as to make the composition so wet that it lacks rigidity. In addition, and as discussed more fully below, the composition can be formed into pellets by an extruding machine and then dehydrated to remove all or a portion of the fluid. Thus, the amount of fluid in the saline solution may be determined, in part, with reference to the extruding machine requirements. For example, and without limitation, some extruding machines require that the composition have a moisture level of between about 12-25% before the composition is formed into a plurality of pellets. Thus, in some embodiments, the amount of fluid may correspond to a composition having a moisture content between about 12-25%. In some examples, and without limitation, after the composition is formed into pellets, they can be dried to have a moisture content of between about 5-18%. Therefore, in some embodiments, the composition can have a moisture content of between about 5-25%

It is preferred that saline solution comprises a fluid that is evaporative at temperatures at or below the temperature at which the composition is dried (which in some embodiments, is about 50 degrees Celsius). However, it is to be appreciated that the saline solution can include other fluids in accordance with some embodiments of the present invention, whether or not they can evaporate below the drying temperature of the composition. For example, the saline solution can include both an evaporative fluid and a non-evaporative fluid.

In some embodiments, and discussed more fully below, the saline solution can be formed by diluting 50 grams of salt in 600 milliliters of distilled water. However, in some embodiments, the amount of salt can be up to 25% by weight in the solution. It is to be appreciated that the amount of salt in the saline solution should be sufficient to prevent dissociation of the methyl farnesoate and the phospholipids but should not be so great such that the use of the composition would present environmental concerns. It has been determined that if the saline solution does not contain sufficient salt, significant loss of concentration of methyl farnesoate can be observed. Thus, in some embodiments, the salt concentration of the saline solution can range between hypotonic body osmotic pressure (<10 ppt or ~330 mOsm) and the concentrations normally found in hypertonic sea water (35-45 ppt or >1000 mOsm). In some preferred embodiments, the salt concentration can be 30 ppt. However, other salt concentrations are contemplated in accordance with some embodiments of the present invention.

In some embodiments, the salt can include sodium chloride, sodium phosphate, calcium phosphate, calcium carbonate, potassium phosphate, potassium sulphate, and potassium chloride, and magnesium oxide. In some embodiments, the salt can include potassium iodide, manganese carbonate, citric acid, ferric citrate, zinc carbonate, and/or cupric carbonate. It is to be appreciated that the saline solution can include a single salt, for example, and without limitation, sodium chloride or calcium phosphate. However, in some embodiments, the saline solution can include a mixture of salts. For example, and without limitation, the saline solution can include a salt combination formed of sodium chloride, sodium phosphate, calcium phosphate, calcium carbonate, potassium phosphate, potassium sulphate, potassium chloride, potassium iodide, magnesium oxide, manganese carbonate, citric acid, ferric citrate, zinc carbonate, and cupric carbonate. In a preferred embodiment, the saline solution can include, by weight, about 3.1% sodium chloride, about 73% calcium phosphate, about 8.1% potassium phosphate, about 6.8% potassium sulphate, about 2.5% magnesium oxide, about 2.1% sodium phosphate, about 2.1% calcium carbonate, about 1.2% ferric citrate, and less than about 1.1% of manganese carbonate, zinc carbonate, cupric carbonate, potassium iodide, and citric acid. However, other salts and combinations of salts are contemplated in accordance with some embodiments of the present invention. For example, and without limitation, a Tomarelli salt mix modified can be used.

In some embodiments, composition can have a pH value of between about 7.8 and about 8.0, which is conductive to liposome stability. Thus in some preferred embodiments, the salt can be calcium phosphate. Calcium phosphate provides buffering which helps maintain a slightly basic pH in a range of about 7.8 to about 8.0. It is to be appreciated that other buffering salts are contemplated in accordance with some embodiments of the present invention.

It is to be appreciated that the dry base and the viscous additive constitute the means for delivering the methyl farnesoate (suspended in the preparation) to the tadpole shrimp and, in some embodiments, constitute nearly the entirety of the composition when dehydrated. It is to be appreciated that the relative amounts of dry base, viscous additive, and fluid (in the saline solution) should be such that, when combined, the mixture has a crumbly consistency, similar to a dry scone or pie dough. It is to be appreciated that the relative percentages of the dry base and the viscous additive affect the consistency of the composition and the ability of pellets which may be formed therefrom to hold their integrity when submerged in water. In some embodiments, the ratio of dry base to viscous additive can be about 90:5. In other embodiments, the ratio of dry base to viscous additive can be about 90:10. It is to be appreciated however, that other ratios are contemplated in accordance with some embodiments of the present invention, depending on the composition of the dry base and the viscous additive. In addition the composition preferably includes between about 1-5 parts of salt, by weight, to about 90 parts dry base. Thus, in some embodiments, the composition can comprise about 90 parts dry base, about 7 parts viscous additive, about 3 parts salt, and significantly less than one part of the preparation comprising the methyl farnesoate. However, it is to be appreciated that other ratios are contemplated in accordance with some embodiments of the present invention.

It is further to be appreciated that the percentages by weight in the composition of the dry base, the viscous additive, and the saline solution may be determined with reference to, among other things, the desired moisture content in the composition. As above, in preferred embodiments, the composition can have a moisture content of between about 12-25% before it is formed into a plurality of pellets and dried. In preferred embodiments, after drying, the composition can have a moisture content of between about 5-18%. Thus in some embodiments, the composition can comprise, by weight, between about 65-85% dry base, between about 5-7% viscous additive, between about 2-3% salt, and between about 5-25% evaporative fluid. In some preferred embodiments, the composition can comprise, by weight, 67.5% dry base, 5.25% viscous additive, 2.25% salt, and 25% distilled water before drying. In other preferred embodiments, the composition can comprise, by weight, 79.2% dry base, 6.16% viscous additive, 2.64% salt, and 12% distilled water before drying. It is to be appreciated that in some embodiments, the contribution of the methyl farnesoate in the final composition can be less than 0.001% by weight.

"Table 1" below illustrates several exemplary combinations of compositions in accordance with some embodiments of the present invention. Rows A-I indicate different combinations, each row listing parts, by weight, of the dry base, the saline solution, and the viscous additive (and compositions thereof). It is to be appreciated that in each of the illustrated examples, the dry base The last row J illustrates preferred ranges for ingredients of compositions in accordance with some embodiments of the present invention.

formed into a plurality of pellets by extrusion processing. Many combinations of ingredients were tested to determine the quality and characteristics of the resulting pellets. The addition of various amounts of certain components affected the overall consistency of the pellets. It was observed that some combinations (not illustrated in "Table 1") created pellets that were too brittle (for example, and without limitation, broke apart easily), too gooey (for example, and without limitation, lacked rigidity and were too malleable), or lacked sufficient integrity when immersed in water (for example, and without limitation, dissolved within a short period of time). For example, too much lecithin results in pellets having a gooey consistency that lack firmness while too little lecithin results in pellets that are brittle and break apart easily.

A first preferred embodiment is the combination of components listed in "Table 1" and identified under Row A. This composition consists of 5 parts gluten, 15 parts white flour, 4 parts Albumin, 10 parts lecithin, 31 parts casein, 25 parts corn starch, 25 parts distilled water, 3 parts salt, 4 parts cod oil, and 3 parts corn oil. This composition has a moisture content of about 20%. The composition can be characterized as having a consistency that allows for the convenient formation of pellets and is not too brittle or powdery to cause excess crumbling. Pellets formed from this composition can be characterized by having substantial integrity when placed in water. Pellets formed from this composition are not too moist, malleable, or gooey such that they would be expected to cause clogging or other problems when used with conventional pellet applicators. Pellets formed from this composition may hold their integrity in water for greater than 5 days.

A second preferred embodiment is the combination of components listed in "Table 1" and identified under Row B. This composition consists of 20 parts white flour, 4 parts Albumin, 10 parts lecithin, 31 parts casein, 25 parts corn starch, 25 parts distilled water, 3 parts salt, 4 parts cod oil, and 3 parts corn oil. This composition also has a moisture content of about 20%. Although this combination lacks gluten, the composition also has a consistency that allows for efficient formation of pellets, and the pellets formed therefrom still have characteristics suitable for application with conventional pellet applicators. Pellets formed from this composition may hold their integrity in water for greater than 5 days.

A third preferred embodiment is the combination of components listed in "Table 1" and identified under Row C. This

TABLE 1

| | Dry base | | | | | | | | Saline | | Viscous | |
| | Gluten | White | | | | | Corn | | | Cod | Corn |
| | Gluten | Flour | Flour | Albumin | Alphacel | Lecithin | Casein | Starch | Fluid | Salt | Oil | Oil |
|---|---|---|---|---|---|---|---|---|---|---|---|---|
| A | 5 | 0 | 15 | 4 | 0 | 10 | 31 | 25 | 25 | 3 | 4 | 3 |
| B | 0 | 0 | 20 | 4 | 0 | 10 | 31 | 25 | 25 | 3 | 4 | 3 |
| C | 0 | 5 | 15 | 4 | 0 | 10 | 31 | 25 | 28 | 3 | 4 | 3 |
| D | 0 | 20 | 0 | 4 | 0 | 10 | 31 | 25 | 28 | 3 | 4 | 3 |
| E | 5 | 15 | 0 | 4 | 0 | 10 | 31 | 25 | 20 | 3 | 4 | 3 |
| F | 5 | 0 | 0 | 4 | 15 | 10 | 31 | 25 | 25 | 3 | 7 | 0 |
| G | 0 | 7.6 | 0 | 4 | 12.4 | 10 | 31 | 25 | 25 | 3 | 3 | 4 |
| H | 0 | 15.2 | 0 | 0 | 10 | 0 | 31 | 25 | 25 | 3 | 1 | 6 |
| I | 0 | 22.8 | 0 | 10 | 10 | 0 | 31 | 25 | 25 | 3 | 0 | 7 |
| J | 0-10 | 0-10 | 10-20 | 3-5 | 0-20 | 0-15 | 20-40 | 10-30 | 13-33 | 1-5 | 0-10 | 0-7 |

In some preferred embodiments, the combinations of components used as shown in "Table 1" can be used to form pellets which have greater integrity when placed in water. It is to be appreciated that the exemplary embodiments of "Table 1" correspond to a composition which may be subsequently composition consists of 5 parts gluten flour, 15 parts white flour, 4 parts Albumin, 10 parts lecithin, 31 parts casein, 25 parts corn starch, 28 parts distilled water, 3 parts salt, 4 parts cod oil, and 3 parts corn oil. This composition has a moisture content of about 22%. While not as good as the first or second preferred embodiments above, the integrity of pellets formed from this composition is good, and may hold their integrity in water for over 4 days. Pellets formed from this composition are also good for application with conventional pellet applicators as they are not too brittle, are not prone to cracking, and do not have a gooey consistency.

A fourth preferred embodiment is the combination of components listed in "Table 1" and identified under Row D. This composition consists of 20 parts gluten flour, 4 parts Albumin, 10 parts lecithin, 31 parts casein, 25 parts corn starch, 28 parts distilled water, 3 parts salt, 4 parts cod oil, and 3 parts corn oil. This composition has a moisture content of about 22%. A fifth preferred embodiment is the combination of components listed in "Table 1" and identified under Row E. This composition consists of 5 parts gluten, 15 parts gluten flour, 4 parts Albumin, 10 parts lecithin, 31 parts casein, 25 parts corn starch, 20 parts distilled water, 3 parts salt, 4 parts cod oil, and 3 parts corn oil. This composition has a moisture content of about 17%. Pellets formed from either the fourth or fifth preferred embodiments exhibit good handling characteristics and are capable of lasting between three to 4 days in water before dissolving.

Additional combinations of components are listed "Table 1" and identified under Rows E-I. Pellets formed from each of these compositions exhibit less than ideal integrity and consistency characteristics. Thus, despite having the same quantity of dry base, viscous additive, salt, and methyl farnesoate, and generally the same quantity of distilled water, pellets formed from these compositions may lack sufficient qualities for use. Pellets formed from these compositions exhibit poor integrity when submersed in water, and these compositions further lack the appropriate consistency for the efficient forming and application of the pellets.

As illustrated in the example corresponding to the last row J included in "Table 1", compositions in accordance with some embodiments can comprise ingredients in the following ranges: 0-10 parts gluten, 0-10 parts gluten flour, 10-20 parts white flour, 3-5 parts albumin, 0-20 parts alphacel, 0-15 parts lecithin, 20-40 parts casein, 10-30 parts corn starch, 13-31 parts distilled water, 1-5 parts salt, 0-10 parts cod oil, and 0-7 parts corn oil. However it is to be appreciated that other amounts of these ingredients are contemplated in accordance with some embodiments of the present invention. For example, and without limitation, the fourth preferred embodiment (corresponding to row D) can be modified to include 15 parts gluten flour, 4 parts Albumin, 15 parts lecithin, 31 parts casein, 25 parts corn starch, 28 parts distilled water, 3 parts salt, 4 parts cod oil, and 3 parts corn oil. It is to be appreciated that the ratio of the dry base to the viscous additive in the above examples is about 90:7 and the ratio of dry base to salt is about 90:3. However, in some embodiments, the exemplary combinations can be modified or scaled such that the ratio of the dry base to the viscous additive is between about 90:5 and about 90:10 and/or the ratio of the dry base to the salt is between 90:1 and 90:5. For example, and without limitation, the fourth preferred embodiment (corresponding to Row D) can be modified to include 7 parts of cod oil instead of 4 parts, and 5 parts of salt instead of 3 parts. As modified, the composition would have about a 90:10 ratio between the dry base and the viscous additive and a 90:5 ratio between the dry base and the salt. However, other modifications are contemplated in accordance with some embodiments of the present invention.

As above, the dry base, the viscous additive, and the saline solution form the means for delivering the methyl farnesoate. In some embodiments, the composition may include a preparation comprising an effective amount of methyl farnesoate.

In some embodiments, the composition can include a minimum of about 0.0001% methyl farnesoate by weight. In some embodiments, the composition can include a maximum of about 0.001% methyl farnesoate by weight. It has been determined that a concentration of as little as about 0.75 micrograms of methyl farnesoate per gram of the final composition is effective for inhibiting sexual development in tadpole shrimp in laboratory conditions. However, even smaller concentrations of methyl farnesoate may prove effective. Thus, in some embodiments, compositions containing at least about 0.30 micrograms of methyl farnesoate per gram of the final composition may be used to reduce sexual development in tadpole shrimp. However, it is to be appreciated that the percentage of methyl farnesoate by weight may be greater or less than these amounts in accordance with some embodiments of the present invention.

In some embodiments, the preparation can also include a pre-liposome for providing the lipid bilayer which protects the methyl farnesoate from degradation and ensures proper distribution of methyl farnesoate throughout the final delivery system. In some embodiments, the pre-liposome can include L-alpha-phosphatidylcholine beta-oleoyl-gamma-palmitoyl and/or cholesterol. It is to be appreciated that a premade liposome product may be used if commercially available. For example, and without limitation, a premade liposome product similar to Formulation 2, #L-3906, previously manufactured by Sigma, can be used. However, it is to be appreciated that other pre-liposomes are contemplated in accordance with some embodiments of the present invention.

In some embodiments, the preparation can also include a solvent for adequately encapsulating the methyl farnesoate in the phospholipid. In some examples, without limitation, and discussed more fully below, the pre-liposome and methyl farnesoate can be dissolved in a solvent. In some examples, and without limitation, the solvent can include ethanol and/or dimethyl sulfoxide. However, it is to be appreciated that other solvents are contemplated in accordance with some embodiments of the present invention.

In some embodiments, a composition containing methyl farnesoate for inhibiting reproduction in tadpole shrimp can include the following components as a delivery means: lecithin-soy refined, casein, wheat gluten, cholesterol, albumin, alphacel, vitamin E acetate, cod liver oil, corn starch, corn oil, L-alpha-phosphatidylcholine beta-oleoyl-gamma-palmitoyl, ethanol or dimethyl sulfoxide, distilled water, sodium chloride, calcium phosphate, potassium phosphate, potassium sulphate, sodium phosphate, and calcium carbonate. It is to be appreciated that all of the above components are not necessary to maintain the methyl farnesoate in a relatively stable state. Accordingly, in some embodiments, a composition can include the following elements: one or more dry ingredients for bulk, binding, and density, one or more oils for adding viscosity, methyl farnesoate, L-alpha-phosphatidylcholine beta-oleoyl-gamma-palmitoyl, ethanol or dimethyl sulfoxide, water, and salt. In some embodiments, the dry ingredients may be selected from one or more of the following: lecithin, casein, gluten, albumin, alphacel, and/or wheat flour. In some embodiments, the oil may comprise vegetable oil, such as, for example, and without limitation, corn oil. In some further embodiments, an attractant and/or nutritional supplement may be added. In some embodiments, the attractant may comprise cod liver oil, shrimp-by product, or any other commonly known attractant known in the art. In some embodiments, the salt may comprise any single salt, combination of salts, or a combination such as those found in Tomarelli Salt Mix Modified.

In some preferred embodiments, a batch of composition can include about 9 kg of dry base, about 760 milliliters of a viscous additive, about 1800 milliliters of water, about 210 grams of salt, and about 600 micro liters of a methyl farnesoate preparation. The dry base can include about 500 grams of wheat gluten, about 1.5 kg of white flour, about 400 grams of albumin, about 1.0 kg of lecithin, about 3.1 kg of casein, and about 2.5 kg of corn starch. The viscous additive can include about 50 grams of cholesterol, about 10 grams of vitamin E Acetate, about 400 milliliters of cod liver oil, and about 300 milliliters of corn oil. The saline solution can include about 1800 milliliters of distilled water, about 86 grams of sodium chloride, about 3.8 grams of calcium phosphate, about 86 grams of potassium phosphate, about 4.08 grams of potassium sulphate, about 1.5 grams of magnesium oxide, about 26 grams of sodium phosphate, and about 1.26 grams of calcium carbonate, about 0.72 grams of ferric citrate, and less than 0.6 grams of manganese carbonate, zinc carbonate, cupric carbonate, potassium iodide, and citric acid. The preparation can include about 221 milligrams of L-alpha-phosphatidylcholine beta-oleoyl-gamma-palmitoyl, about 78 milligrams of cholesterol, between about 0.01 grams and about 0.1 grams of methyl farnesoate, and about 200 micro liters of either ethanol or dimethyl sulfoxide (DMSO) solution. However, it is to be appreciated that the batch size can be increased or decreased by proportionally increasing or decreasing the above listed amounts. It is further to be appreciated that variations of the ingredients and/or amounts listed are contemplated in accordance with some embodiments of the present invention. For example, and without limitation, one or more of the above listed amounts can be increased or decreased by 10%.

Exemplary Methods for Making Compositions

In some embodiments, the invention concerns methods of making any of the compositions described above which can include first preparing or selecting each of the dry base, the viscous additive, the saline solution, and the methyl farnesoate preparation. Then, the dry base and the viscous additive can be combined to form a homogenous first mixture. In some embodiments, a first portion of the saline solution can be added to the homogenous first mixture, and a second portion of the saline solution can be added to the methyl farnesoate preparation to form a second mixture. In other embodiments, the entirety of the saline solution can be combined with the methyl farnesoate preparation to form a second mixture which can then be added to the homogenous first mixture. In some other embodiments, the entirety of the saline solution can be added to the homogenous first mixture, and a second saline solution can be prepared and combined with the methyl farnesoate preparation which may then be added to the first saline solution/dry base/viscous additive combination. In some embodiments, the composition may then be formed into pellets and dried. It is to be appreciated that the following discussion may include one or more exemplary illustrations of ingredients and/or the relative or absolute amounts of such ingredients of the dry base, the viscous additive, the saline solution, and the methyl farnesoate preparation. However the exemplary ingredients and amounts may be varied in accordance with some embodiments of the present invention.

In some embodiments, preparing the dry base can include selecting and/or combining one or more ingredient(s). In some embodiments where the dry base includes more than one ingredient, those ingredients may be mixed to create a homogenous dry mixture. In some embodiments, in order to ensure homogenous mixing, the ingredients should be blended for a suitable time. For example, and without limitation, the dry ingredients can be mixed for about thirty (30) minutes. However, it is to be appreciated that the time required to obtain a homogeneous composition can be more or less, depending among other things on the method and speed of blending.

In some embodiments, the dry base can include one or more of wheat gluten, wheat flour, white flour, corn flour, albumin, alphacel, corn starch, casein, lecithin, attractants (such as, for example, fish byproducts and organic matter), vitamins, and/or nutritional supplements. In some examples, and without limitation, an exemplary batch of the inhibiting composition can include 9 kilograms of a dry base, prepared by combining about 500 grams of wheat gluten, about 1.5 kg of white flour, about 400 grams of albumin, about 1.0 kg of lecithin, about 3.1 kg of casein, and about 2.5 kg of corn starch. In some other examples, an exemplary batch of the inhibiting composition can include 9 kilograms of a single bulk ingredient, such as wheat flour.

In some embodiments, preparing the viscous additive can include, separately from preparing the dry base, selecting and/or combining together one or more oily compounds. In some embodiments the oily compounds can include one or more of fish oils, cod liver oil, vegetable oils, cholesterol, vitamin E Acetate. In some examples, and without limitation, an exemplary batch of the inhibiting composition can include 760 milliliters of a viscous additive, prepared by combining about 50 grams of cholesterol, about 10 grams of vitamin E Acetate, about 400 milliliters of cod liver oil, and about 300 milliliters of corn oil. In some other examples, an exemplary batch of the inhibiting composition can include about 700 milliliters of a single oily compound, such as cod liver oil.

In some embodiments, after the dry base and the viscous additive have been prepared, they may be combined together to form a homogenous first mixture. It is to be appreciated that that the dry base and the viscous additive be combined together before the saline solution and methyl farnesoate are added. Adding methyl farnesoate directly to the dry base may result in the loss or destruction of the methyl farnesoate due to oxidative processes and/or shearing forces occurring during the step of forming the first mixture. Adding methyl farnesoate directly to the viscous additive may result in the loss or destruction of the methyl farnesoate due to liposome disassembly. Furthermore, adding the saline solution directly to the dry base may not fully protect the methyl farnesoate once it is added. In some examples, and without limitation, an exemplary batch of the inhibiting composition can be prepared by forming a first mixture by combining about 9 kilograms of dry base and about 700 milliliters of viscous additive. However, it is to be appreciated that other amounts of dry base and/or viscous additive are contemplated in accordance with some embodiments of the present invention.

As above, in some embodiments, attractants, vitamins, and/or nutrients may be included in the dry base and/or viscous additive preparations. For example, and without limitation, vitamins can be blended with the dry base and attractants may be blended with the viscous additive before the combining thereof. However, in some embodiments, attractants, vitamins, and/or nutritional supplements can be simultaneously combined with the dry base and viscous additive in one step. In some other embodiments, the dry base and viscous additive can first be combined, and then the attractants, vitamins, and/or nutritional supplements can be added thereto. However, it is to be appreciated that any subsequently added ingredients must be thoroughly incorporated into the first mixture prior to introduction of the methyl farnesoate.

In some embodiments, separate from the creation of the first mixture is the creation of the saline solution and the methyl farnesoate preparation. In some examples, and without limitation, the saline solution and/or methyl farnesoate preparation can be obtained commercially. In other examples, one or both of them may be prepared.

In some embodiments, the methyl farnesoate preparation can be prepared by vigorously agitating the methyl farnesoate, a pre-liposome, and a solvent. In some embodiments, the methyl farnesoate preparation can be prepared by first combining the methyl farnesoate and pre-liposome and is strongly agitating. In some embodiments, the amount of methyl farnesoate can be between about 0.0001% and 0.001% by weight relative to the composition. In some embodiments, the pre-liposome can comprise L-alpha-phosphatidylcholine beta-oleoyl-gamma-palmitoyl and cholesterol. In some examples, and without limitation, an exemplary batch of the inhibiting composition can include a methyl farnesoate preparation, prepared by combining between about 0.01 grams and about 0.1 grams of methyl farnesoate, about 221 milligrams of L-alpha-phosphatidylcholine beta-oleoyl-gamma-palmitoyl, and about 78 milligrams of cholesterol. It is to be appreciated that the mixture of methyl farnesoate, the L-alpha-phosphatidylcholine beta-oleoyl-gamma-palmitoyl, and the cholesterol should be thoroughly combined to obtain even distribution. It is further to be appreciated that more or less than the amount of pre-liposome listed above can be provided. In some examples, and without limitation, the methyl farnesoate can be mixed with up to 15% more, or 15% less, L-alpha-phosphatidylcholine beta-oleoyl-gamma-palmitoyl and cholesterol.

In some embodiments, after the methyl farnesoate and the pre-liposome (which can include, for example and without limitation, L-alpha-phosphatidylcholine beta-oleoyl-gamma-palmitoyl and cholesterol) are thoroughly combined, they can then dissolved into a solvent. In some embodiments, the solvent can include ethanol and/or dimethyl sulfoxide. In some examples, and without limitation, a ten kilogram batch of the inhibiting composition can be prepared by dissolving between about 0.01 grams and about 0.1 grams of methyl farnesoate, about 221 milligrams of L-alpha-phosphatidylcholine beta-oleoyl-gamma-palmitoyl, and about 78 milligrams of cholesterol in about 200 micro liters of either ethanol or dimethyl sufoxide. In some embodiments, vigorously vortexing or agitating the methyl farnesoate, pre-liposome, and solvent will ensure more homogenous liposome sizes. It is further to be appreciated that more or less than the amount of solvent listed above can be provided. In some examples, and without limitation, the methyl farnesoate and pre-liposome can be dissolved in up to 15% more, or 15% less, solvent.

It is to be appreciated that, in some embodiments, the integrity of the phospholipid-encapsulated methyl farnesoate when incorporated into the first mixture is maintained by, and the ability for the composition to be formed into pellets is provided by, a saline solution. In some aspects, the salinity of the solution serves to prevent the separation of the lipid bilayers by increasing the osmotic pressures incident thereon. Thus, in some embodiments, the amount of salt in the saline solution can be between 0.1% and 25% by weight. In some embodiments, the saline solution can be prepared by dissolving up to 1 parts of a salt in up to 3 parts of a fluid. It is to be appreciated that the amount of fluid provided in the saline solution is a function of the amount of dry base and viscous additive, levels of moisture in the dry ingredients, and ambient humidity levels in the air, among other factors. In addition, the amount of fluid provided in the saline solution can be a function of the desired moisture content in the composition. As above, below, in some embodiments, the composition may be extruded to form a plurality of pellets. Some typical commercial extruding machines require between 12-25% moisture content to adequately form pellets. Thus, in some embodiments, the amount of fluid in the saline solution can correspond to an amount required to form a composition having between about 12-25% moisture content. However, it is to be appreciated that even if the extruding processes employed suggest moisture contents below 12%, the amount of fluid in the solution should not be too low or the phospholipid-encapsulated methyl farnesoate risks being destroyed when combined with the dry base and viscous additives.

As above, in some embodiments, the fluid may be distilled water or any other fluid which evaporates at or below the temperature at which pellets that can be formed of the composition are dried. However, in some embodiments, the saline solution may also include a fluid which does not evaporate at or below the temperature at which the pellets are dried. In some embodiments, the saline solution can be formed by dissolving in the fluid a single salt, such as calcium phosphate. However, in some embodiments, the saline solution can be formed by dissolving in the fluid a combination of salts, such as for example, and without limitation, sodium chloride, sodium phosphate, calcium phosphate, calcium carbonate, potassium phosphate, potassium sulphate, potassium chloride, and or magnesium oxide. In some embodiments, the salt can further include potassium iodide, manganese carbonate, citric acid, ferric citrate, zinc carbonate, and/or cupric carbonate. However, other salts and combinations of salts are contemplated in accordance with some embodiments of the present invention. In a preferred embodiment, the saline solution can include, by weight, about 3.1% sodium chloride, about 73% calcium phosphate, about 8.1% potassium phosphate, about 6.8% potassium sulphate, about 2.5% magnesium oxide, about 2.1% sodium phosphate, about 2.1% calcium carbonate, about 1.2% ferric citrate, and less than about 1.1% of manganese carbonate, zinc carbonate, cupric carbonate, potassium iodide, and citric acid. In some examples, and without limitation, an exemplary batch of the inhibiting composition can be prepared by dissolving in about 1800 milliliters of distilled water about 86 grams of sodium chloride, about 3.8 grams of calcium phosphate, about 86 grams of potassium phosphate, about 4.08 grams of potassium sulphate, about 1.5 grams of magnesium oxide, about 26 grams of sodium phosphate, and about 1.26 grams of calcium carbonate, about 0.72 grams of ferric citrate, and less than about 0.6 grams of manganese carbonate, zinc carbonate, cupric carbonate, potassium iodide, and citric acid.

After the first mixture (comprising the dry base, the viscous additive, and optionally, the attractants, vitamins, and/or nutritional supplements), the saline solution and the second mixture (including the methyl farnesoate preparation) have been created, the composition may be formed. In some preferred embodiments, the composition can be formed by first adding all or a portion of the saline solution to the first mixture. In these embodiments, after the saline solution is added, the first mixture should have a consistency which can be described as "crumbly" or "clumpy" after the saline solution is incorporated therein. The first mixture should neither be too dry, nor too wet, nor too powdery, nor resemble a smooth batter, but in contrast should resemble that of a dry scone or pie dough. A complete lack of moisture in the first mixture can be disruptive to the methyl farnesoate, when subsequently added, and may result in undesirably low concentrations in the end product. A first mixture which is too powdery (or too dry) could result in the methyl farnesoate being destroyed after it is subsequently added, rendering the resulting composition useless for effectively affecting the reproductive systems of the pests. If the first mixture is too wet, the step of forming the composition into pellets becomes difficult and may both increase costs due to longer drying periods and create further problems in the process of applying the formed pellets to temporary pools. Thus, sufficient moisture should be present to obtain a consistency conducive to preserving the methyl farnesoate when added. In some embodiments, if the first mixture appears powdery or if it is otherwise determined that the first mixture does not have the desired moisture content, more liquid (such as distilled water) may be added to obtain a clumpy or crumbly consistency. In some embodiments, if the first mixture appears to be too wet, more dry ingredients, such as starch, flour, alphacel, and/or the like may be added to obtain a clumpy or crumbly consistency.

In some embodiments, after the saline solution is added to and fully combined with the first mixture, the methyl farnesoate preparation can be added to finally form the composition. In some embodiments, the methyl farnesoate preparation can be added directly to the first mixture. In some other embodiments, a second mixture including the methyl farnesoate preparation can be formed, and the second mixture can be added to the first mixture. It is to be appreciated that after the saline solution has been added to the dry base/viscous fluid combination, there should be sufficient salt to prevent the lipid bilayers of the phospholipid-encapsulated methyl farnesoate from dissociating. However, additional liposome protection may be provided by buffering the methyl farnesoate preparation with a portion of the first saline solution, or optionally, a second saline solution. Thus, in some embodiments, the second mixture may be formed by adding a second portion of the first saline solution to the preparation. In some embodiments, before the first saline solution is added to the first mixture, a small amount may be set aside or reserved and added to the methyl farnesoate preparation. In some embodiments, only a small fraction of the first saline solution need be added to the methyl farnesoate preparation. For example, and without limitation, 50 milliliters may be sufficient. However, it is to be appreciated that any fraction of the first saline solution may be used in accordance with some embodiments of the present invention. For example, up to half of the first saline solution can be added to the first mixture and up to half can be added to the methyl farnesoate preparation.

In some embodiments, additional salt may be added to the first or second portions of the saline solution provide different salinities thereof. For example, and without limitation, it may be desired to provide a second mixture with a higher salinity than the saline solution to ensure adequate liposome protection. Thus, in some preferred embodiments, the methyl farnesoate preparation is combined with a first saline solution having a concentration of salt of about 0.1% to 10% salt by weight. Subsequently, additional salt can be added to the second mixture to bring the total salinity of the second mixture to a desired value. In some embodiments, the total salinity of the second mixture may be gradually increased from about 0.1% to about 25% by weight. In a similar fashion, in some examples, it may be desired to provide a second mixture with a lower salinity of the saline solution. In some embodiments, after the second portion of the saline solution is reserved, additional salt can be added to the first portion. Alternatively, the second mixture can be diluted by adding additional distilled water. However, other ways of adjusting the relative salinities are contemplated in accordance with some embodiments of the present invention.

In some embodiments, instead of adding a second portion of the first saline solution to the methyl farnesoate preparation, a second saline solution can be prepared. In some embodiments, the second saline solution can be formed of the same fluid and/or salt as the first saline solution, as discussed above. However, in other embodiments, different fluid and/or salts may be used. For example, and without limitation, the salt included in the first saline solution can be calcium phosphate and the salt included in the second saline solution can be sodium chloride. Similarly, the first and second saline solution need not have the same salinity. For example, and without limitation, the first saline solution can comprise about 10% salt by weight while the second saline solution can comprise up to about 25% salt by weight. It is to be appreciated however that the second saline solution can comprise other salts and in different concentrations in some embodiments of the present invention.

It is to be appreciated that other ways of combining the dry base, the viscous additive, the evaporative fluid, the salt, and the methyl farnesoate preparation are contemplated in accordance with some embodiments of the present invention. For example, and without limitation, instead of first adding the saline solution to the dry base/viscous fluid combination, all of the saline solution can be admixed with the methyl farnesoate preparation. In some examples, the saline solution and the viscous additive can first be combined to form an emulsion, then added to the dry base, and thereafter the methyl farnesoate can be added. However, it is important to appreciate that adding the methyl farnesoate preparation directly added to the dry base would result in the destruction of the phospholipid-encapsulated methyl farnesoate by shearing forces. It is also important to appreciate that adding the methyl farnesoate preparation directly to the viscous additive could also destroy the phospholipid-encapsulated methyl farnesoate by shearing forces, as well as destroy the lipid-bilayers.

In some embodiments of the present invention, the composition should be formed such that it is capable of being readily consumed by the target pests while at the same time resisting rapid dissolution or decay. Thus, in some embodiments, the composition can further be formed into a plurality of readily consumable particles. The particles need not be of any specific size or shape, however it can be appreciated that the size and shape of the particles may affect the overall solubility of the composition, the ability of the target pests to consume the particles, and the type of devices which may be used to dispense the particles into the temporary pools. Additionally, although larger pellets may last longer under water, they may cost more to manufacture. Thus, the size and shape of the particles is a significant factor in successfully inhibiting the ovarian development of the target pests. Therefore, in some preferred embodiments, the compositions can be formed into particles having sizes and shapes selected such that they can remain submerged in water without dissolving for an amount of time necessary for the tadpole shrimp to hatch and eat a sufficient amount of the composition containing methyl farnesoate.

In some embodiments, the composition can be formed into a shape such as pellets, orbs, cylinders, nuggets, discs, or crystals. It is to be appreciated that the particles should contain available surfaces upon which the target pests can feed. In some preferred embodiments, the composition may be formed into particles having corners, contours or edges that may be easily received into the mouth of a target pest. In addition to the shape of the particles, the size of the particles may be selected so that they may be received into the mouth of a target pest.

The mouths of tadpole shrimp range in sizes from about 0.1 mm for juvenile shrimp to about 4 mm or greater for mature shrimp. Thus, in some preferred embodiments, the composition may be formed into particles having a diameter of between about 1 mm to 6 mm. It is to be appreciated that particles having larger sizes may not immediately be consumed by juvenile or some mature tadpole shrimp. However, after a period of time has elapsed, unconsumed particles may degrade and/or dissolve in the water, at which time they may be readily consumed by the tadpole shrimp. Further, it is to be appreciated that tadpole shrimp have an elongate pre-digestive track. Thus, in some preferred embodiments, the composition may be formed into cylindrical particles. In some preferred embodiments, the cylindrical particles may have radii between about 1 mm and 6 mm and lengths of between about 4 and about 20 millimeters.

In some embodiments, the particles may be formed by a commercial pellet extruder or a commercial pasta maker to ensure roughly uniform particle size. However, in some applications, particles having non-uniform sizes may be preferred. For example, and without limitation, particles having variable sizes may be used to provide a longer effective time frame: smaller particles may be consumed and dissolve first, while larger particles may last longer and be consumed later. As such, the target pests may be exposed to the methyl farnesoate composition for a prolonged period of time.

In some further embodiments, the particles once formed can be dried to have a moisture content of, for example, about 5% and about 18%. Drying the particles assist in the efficient packaging, distribution, and dispensing of the particles. During such drying, the particles should not be exposed to extreme heat, which could reduce methyl farnesoate concentrations. Exposure to temperatures above about 50 degrees Celsius may cause significant loss of methyl farnesoate concentration from the pellets. Thus, in some embodiments, the pellets may be dried at a temperature below about 50 degrees Celsius. In some embodiments, relatively lower temperature drying can be enhanced by circulating ambient air over the particles.

In some further embodiments, the particles may be coated to further prevent them from quickly dissolving or dissipating once exposed to water. In some examples, and without limitation, the particles may be coated in a protein. In some examples, the particles may be coated in a semi-permeable membrane. It is to be appreciated however that other coatings are contemplated in accordance with some embodiments of the present invention It is to be appreciated that the methods of making the compositions in accordance with some embodiments of the present invention may include a wide variety and quantities of different dry ingredients, a wide variety and quantities of different oily ingredients, and a wide variety and quantities of different salt. It is also to be appreciated that in accordance with some embodiments of the present invention any of these methods may include the optional addition of one or more attractants, one or more buffers, and/or one or more binding agents. It is also to be appreciated that in accordance with some embodiments of the present invention the final products may be provided in a wide variety of different sizes and/or shapes, or in uniform sizes and/or shapes, depending on the application. It is also to be appreciated that in accordance with some embodiments of the present invention the drying time for the final products may vary greatly depending on the initial moisture content, temperature used, the size of the individual product items themselves, humidity and other similar factors.

Exemplary Methods for Using Compositions

It is to be appreciated that the primary target of the present is the tadpole shrimp, which subsist in tiny cysts in dry temporary pools, such as rice fields, until water is applied. The tadpole shrimp begin to hatch within two to three days of the flooding of the pools. Accordingly, application of methyl farnesoate laced particles in accordance with embodiments of the present invention before or immediately after flooding ensures that the particles, and thus methyl farnesoate will be available for the juvenile tadpole shrimp to consume. Continued consumption of methyl farnesoate laced pellets over a period of several days will inhibit the reproductive activity of the tadpole shrimp. Typically, tadpole shrimp become reproductive after 4 days post-hatch and the majority of the tadpole shrimp will die off after 12-15 days. Thus, it is important that the particles will not degrade (or if they degrade, will quickly be replaced) during this critical time frame (e.g., from about 4 days to about 2 weeks after flooding of the temporary pools). Thus, in some embodiments, the invention concerns a method for inhibiting the reproductive activity of tadpole shrimp which can include the step of dispensing any of the particles described above into a field where the tadpole shrimp, eggs of the tadpole shrimp and/or cysts of the tadpole shrimp are present.

In some embodiments, the particles can be dispensed prior to flooding the field with water. If the particles are heavy enough (for example, and without limitation, have sufficient bulk and/or oil content), they will not be washed away upon the flooding of the temporary pools. For example, and without limitation, the particles can be applied to rice fields in the early season to inhibit tadpole shrimp reproduction during the planting and early growth of the rice crop. It is to be appreciated however that depending on the climate, the particles should not be applied too early in the season as humidity and heat may degrade the particles (and thus the methyl farnesoate) before the tadpole shrimp have a change to consume them. In some embodiments, the particles may be applied to the rice fields immediately prior to flooding. It is to be appreciated that in these embodiments, the particles need to withstand dissolving for a long enough time in order to allow the tadpole shrimp to first hatch and begin feeding (which in some examples, and without limitation, may take two to three days).

In other embodiments, the particles can have a density sufficiently greater than water and may be dispensed after the flooding of the field. For example, and without limitation, the particles can be applied to rice fields immediately after flooding to inhibit reproduction of tadpole shrimp. It is to be appreciated however that the particles should be applied relatively shortly after the fields are flooded so that they will be available for the tadpole shrimp to consume them upon hatching (which in some examples, and without limitation, may take two to three days).

In some embodiments, the particles should remain structurally and chemically stable in the field for between about 4 days and about 14 days after their exposure to water. However, in some embodiments, if the particles cannot remain stable during this time period, or if the initial application of particles is not sufficient, further application of additional particles may be required to effectively inhibit the reproduction of the tadpole shrimp. Additionally, when the temperature of the water is cold, tadpole shrimp may take longer to hatch. Thus, particles for use in such applications must be able to withstand degradation for longer periods of time.

Initial experiments have shown that applications of at least about two grams per square foot of particles in accordance with some embodiments of the present invention are sufficient to inhibit ovarian development of tadpole shrimp. Thus, in some embodiments, the particles may be dispensed at a concentration of about 2 grams per square foot. However, it is to be appreciated that higher or lower concentrations are contemplated in accordance with some embodiments of the present invention. For example, and without limitation, depending on the severity of the tadpole shrimp populations greater or lesser concentration of particles may be required to inhibit the tadpole shrimp reproduction.

The particles may be dispensed by conventional means, such as by plane or by fertilizer applicators. In some preferred embodiments, the particles can be dispensed by aerial application after the temporary pools have been flooded. In some preferred embodiments, the particles can be dispensed by fertilizer applicators before the temporary pools have been flooded. It is to be appreciated that the population of the target pest will be gradually reduced over time. In some preferred embodiments, additional particles can be applied to the temporary pool at least once during a flooding/drying cycle of the temporary pool and successively thereafter during each flooding/drying cycle. For example, and without limitation, (i) some particles can be dispensed immediately before or after flooding the temporary pool, (ii) the crop can be grown and harvested, (iii) the temporary pool can be allowed to at least partially dry out, and (iv) the cycle can be repeated beginning first with the application of additional particles immediately before or after the temporary pool is re-flooded. However, other treatment plans are contemplated in accordance with some embodiments of the present invention.

Preferred Embodiments of the Present Invention

In some preferred embodiments, inhibiting the reproductive activity of tadpole shrimp in a field can include the steps of (i) forming a plurality of mixtures, solutions, and/or combinations, (ii) forming a composition from the mixtures, solutions, or combinations, (iii) forming particles from the composition, (iv) drying the particles, and (v) dispensing the particles in the field.

In a first preferred embodiment, a dry base may be formed by combining flour, gluten, albumin, alphacel, casein, lecithin, and/or starch. A viscous additive may be formed by combining one or more oils such as fish oil and/or vegetable oil. A medium may be formed by combining the dry base, the viscous additive, and optionally, an attractant such as lecithin, casein, vitamin E acetate, cholesterol, fish extract, fish byproduct, crustacean extract, crustacean byproduct, and/or organic matter. A saline solution may be formed by dissolving in distilled water sodium chloride, sodium phosphate, calcium phosphate, calcium carbonate, potassium phosphate, potassium sulphate, potassium chloride, magnesium oxide, and/or ferric citrate. A preparation may be formed of methyl farnesoate, a pre-liposome such as L-alpha-phosphatidylcholine beta-oleoyl-gamma-palmitoyl and cholesterol, and a solvent such as ethanol, dimethyl sulfoxide, and combinations thereof.

In some embodiments, a first intermediate mixture may be formed by combining a first portion of the saline solution and the medium. A second intermediate mixture may be formed by combining a second portion of the saline solution and the preparation. A composition having a moisture content of greater than about 10% may be formed by combining the first and the second intermediate mixtures.

In some embodiments, a plurality of particles having a dimension of between about 1 and about 6 millimeters may be formed from the composition. The particles may be dried to have a moisture content of less than about 20%. The dried particles may have a methyl farnesoate concentration of between about 0.0001% and about 0.001% by weight. The dried particles may then be dispensed at a concentration of about 2 grams per square foot into a field where the tadpole shrimp, the eggs of the tadpole shrimp, and/or the cysts of the tadpole shrimp are present.

In a second preferred embodiment, a dry base may be formed by combining flour, gluten, albumin, alphacel, casein, lecithin, and/or starch. A viscous additive may be formed by combining one or more oils such as fish oil and/or vegetable oil. A first mixture may be formed by combining the dry base, the viscous additive, and optionally, an attractant such as lecithin, casein, vitamin E acetate, cholesterol, fish extract, fish byproduct, crustacean extract, crustacean byproduct, and/or organic matter. A first saline solution may be formed by dissolving in distilled water sodium chloride, sodium phosphate, calcium phosphate, calcium carbonate, potassium phosphate, potassium sulphate, potassium chloride, magnesium oxide, and/or ferric citrate. A second saline solution may be formed by dissolving in distilled water sodium chloride, sodium phosphate, calcium phosphate, calcium carbonate, potassium phosphate, potassium sulphate, potassium chloride, magnesium oxide, and/or ferric citrate. A preparation may be formed of methyl farnesoate, a pre-liposome such as L-alpha-phosphatidylcholine beta-oleoyl-gamma-palmitoyl and cholesterol, and a solvent such as ethanol, dimethyl sulfoxide, and combinations thereof.

In some embodiments, a composition having a moisture content of greater then about 10% may be formed by first combining the first saline solution and the first mixture, and then adding thereto a second mixture comprising the preparation and the second saline solution forming a plurality of particles from said composition, wherein said particles have a dimension of between about 1 and about 6 millimeters;

In some embodiments, a plurality of particles having a dimension of between about 1 and about 6 millimeters may be formed from the composition. The particles may be dried to have a moisture content of less than about 20%. The dried particles may have a methyl farnesoate concentration of between about 0.0001% and about 0.001% by weight. The dried particles may then be dispensed at a concentration of about 2 grams per square foot into a field where the tadpole shrimp, the eggs of the tadpole shrimp, and/or the cysts of the tadpole shrimp are present.

In a third preferred embodiment, a first intermediate mixture may be formed by combining about 5 parts gluten, about 15 parts white flour, about 4 parts albumin, about 10 parts lecithin, about 31 parts casein, about 25 parts corn starch. A second intermediate mixture may be formed by combining about 4 parts cod liver oil and about 3 parts corn oil. A first intermediate solution may be formed by combining about 3 parts of a salt dissolved in at least about 13 parts distilled water, wherein said salt comprises about 3.1% sodium chloride, about 73% calcium phosphate, about 8.1% potassium phosphate, about 6.8% potassium sulphate, about 2.5% magnesium oxide, about 2.1% sodium phosphate, about 2.1% calcium carbonate, about 1.2% ferric citrate, and less than about 1% of manganese carbonate, zinc carbonate, cupric carbonate, potassium iodide, and citric acid. A second intermediate solution may be formed by vigorously agitating an effective amount of methyl farnesoate, L-alpha-phosphatidylcholine beta-oleoyl-gamma-palmitoyl, cholesterol, and a solvent such as ethanol and/or dimethyl sufoxide.

In some embodiments, a third intermediate mixture may be formed by combining the first and the second intermediary mixtures. Then separately (i) combining a first amount of the first intermediate solution and the third intermediate mixture to form a fourth intermediate mixture having a crumbly consistency and having a moisture content of between about 12% and about 25% and (ii) adding a second amount of the first intermediate solution to the second intermediate solution. Then, a composition may be formed by combining the fourth intermediate mixture and the second intermediate solution.

In some embodiments, a plurality of pellets may then be formed from the composition by extrusion processing. The pellets may be cylindrical, may have a diameter of between about 1 mm and about 6 mm, and may have a length of about 4 mm and about 20 mm. The plurality of pellets may then be dried to have a moisture content of between about 5% and about 18%. The dried pellets may have a methyl farnesoate concentration of between about 0.0001% and about 0.001% by weight. The dried pellets may then be dispensed into a temporary pool at a concentration of about 2 grams per square foot.

In a fourth preferred embodiment, a first intermediate mixture may be formed by combining between about 67 parts and about 80 parts of a dry ingredient and between about 5 parts and about 7 parts of an oily compound. The dry ingredient may include flour, gluten, albumin, alphacel, casein, lecithin, and/or starch. The oily compound may be fish oil and/or vegetable oil. A first intermediate solution having a first and as second portion may be formed by combining between about 2 parts and about 3 parts of a salt and between about 12 parts and about 25 parts of water. The salt may include sodium chloride, sodium phosphate, calcium phosphate, calcium carbonate, potassium phosphate, potassium sulphate, potassium chloride, magnesium oxide, and/or ferric citrate. A second intermediate solution may be formed by (i) vigorously agitating an effective amount of methyl farnesoate, L-alpha-phosphatidylcholine beta-oleoyl-gamma-palmitoyl, cholesterol, and a solvent such as ethanol and/or dimethyl sufoxide, and (ii) adding thereto the second portion of the first intermediary solution, saline, water, and/or salt.

In some embodiments, the first portion of the first intermediate solution can be added to the first intermediate mixture to form a second intermediate mixture having a crumbly consistency. Then, a composition having a moisture content of between about 12% and about 25% may be formed by combining the second intermediate mixture and the second intermediate solution.

In some embodiments, a plurality of pellets may then be formed by extrusion processing. The pellets may have a diameter of between about 1 mm and about 6 mm and have a length of about 4 mm and about 20 mm. The plurality of pellets may then be dried to have a moisture content of between about 5% and about 18%. The dried pellets may have a methyl farnesoate concentration of between about 0.0001% and about 0.001%. The pellets may then be dispensed into a temporary pool.

The present invention provides compositions and methods for making and using the compositions which provide an environmentally and economically efficient approach to controlling tadpole shrimp in temporary pools. However, it is to be appreciated that the invention may be practiced to control other pests which dwell in temporary pools. It is to be understood that variations and/or modifications of the present invention may be made without departing from the scope of thereof. It is also to be understood that the present invention is not to be limited by the specific embodiments, descriptions, or illustrations or combinations of either components or steps disclosed herein. Thus, although various process parameters (including but not limited to amounts, percentages, concentrations, times, temperatures, pressures, volumes, humidity, and the like) were provided in conjunction with one or more examples, it is to be appreciated that these parameters are exemplary and are not meant to limit the scope of the present invention.

What is claimed is:

1. A method of making a composition consisting of the steps of:
   a. combining to form a homogenous first mixture (i) a dry base consisting of gluten, flour, albumin, lecithin, casein, and corn starch and (ii) a viscous additive comprising an oily compound;
   b. adding a first portion of a saline solution consisting of distilled water and sodium chloride to said first mixture to form a crumbly consistency;
   c. adding a second mixture consisting of a preparation of an effective amount of methyl farnesoate encapsulated in phospholipids to said first mixture;
   d. forming said composition into a plurality of particles; and
   e. drying said particles.

2. The method of claim 1, wherein said oily compound comprises one of the group consisting of fish oil, vegetable oil, and combinations thereof.

3. The method of claim 1, wherein said preparation was formed by vigorously agitating said methyl farnesoate, a pre-liposome and a solvent.

4. The method of claim 3, wherein said pre-liposome comprises L-alpha-phosphatidylcholine beta-oleoyl-gamma-palmityol and cholesterol.

5. The method of claim 3, wherein said solvent comprises one of the group consisting of ethanol, dimethyl sulfoxide, and combinations thereof.

6. The method of claim 1, wherein the shape of said particles is selected from the group consisting of pellets, orbs, cylinders, nuggets, discs, and crystals.

7. The method of claim 1, wherein each of said particles has a diameter of between about 1 and about 6 millimeters.

8. The method of claim 1, wherein said particles are dried to a moisture content of between about 5% and about 25%.

9. The method of claim 1, wherein said particles are dried at a temperature of less than about 50 degrees Celsius.

* * * * *